United States Patent [19]

Schwab

[11] Patent Number: 4,706,057
[45] Date of Patent: Nov. 10, 1987

[54] MAGNET OF A NUCLEAR SPIN TOMOGRAPH

[75] Inventor: August Schwab, Berlin, Fed. Rep. of Germany

[73] Assignee: Siemens Aktiengesellschaft, Berlin and Munich, Fed. Rep. of Germany

[21] Appl. No.: 860,627

[22] Filed: May 7, 1986

[30] Foreign Application Priority Data

May 23, 1985 [DE] Fed. Rep. of Germany ....... 3518852

[51] Int. Cl.$^4$ .............................................. H01F 13/00
[52] U.S. Cl. ................................... 335/284; 335/301; 335/304
[58] Field of Search .............. 335/284, 301, 302, 304, 335/306; 324/318, 320, 321

[56] References Cited

U.S. PATENT DOCUMENTS

| 3,927,397 | 12/1975 | Chow et al. .................. 340/174 TF |
| 4,614,930 | 9/1986 | Hickey et al. .................. 335/306 X |

FOREIGN PATENT DOCUMENTS

| 1283976 | 11/1968 | Fed. Rep. of Germany ...... 335/306 |
| 2605666 | 8/1976 | Fed. Rep. of Germany ...... 335/296 |
| 985815 | 7/1951 | France ................................. 335/284 |
| 1047700 | 12/1953 | France ................................. 335/272 |
| 1125874 | 11/1956 | France ................................. 335/306 |
| 2549281 | 1/1985 | France . |
| 298777 | 8/1965 | Netherlands ........................ 335/296 |
| 8400611 | 2/1984 | PCT Int'l Appl. ................. 335/297 |
| 8401226 | 3/1984 | PCT Int'l Appl. . |

OTHER PUBLICATIONS

R. E. Jones, Jr., *IBM Technical Disclosure Bulletin*, "Directionally Homogeneous Magnets for Vacuum-Deposition Apparatus", vol. 19, No. 5, pp. 1856-1857, Oct. 1976.

Primary Examiner—George Harris
Attorney, Agent, or Firm—Kenyon & Kenyon

[57] ABSTRACT

A magnet of permanent magnet material for use in a nuclear spin tomograph has a longitudinally extending cavity for receiving a patent, the cavity and the outer contour of the magnet being substantially rectangular. The magnet comprises simple prismatic parts which are assembled unmagnetized. Upon assembly, the magnet is magnetized so that an approximately homogeneous magnetic field prevails in the cavity and the space outside the magnet is approximately free of fields. Magnetically soft plates are disposed on the inside surfaces of two horizontal legs of the magnet.

14 Claims, 2 Drawing Figures

MAGNET OF A NUCLEAR SPIN TOMOGRAPH

BACKGROUND OF THE INVENTION

This invention relates to a magnet for use in a nuclear spin tomograph and more particularly to such a magnet having an opening which extends in a longitudinal direction and forms a cavity for receiving a patient, the magnet generating in the cavity an approximately homogeneous magnetic field which is perpendicular to the longitudinal axis of the magnet.

Such a magnet is disclosed in published PCT patent application WO-Al No. 84/01 226. The disclosed magnet generates a homogeneous magnetic field, wherein the relative inhomogeneity is $5 \times 10^{-4}$. Outside the magnet, only a small stray field is generated, the major part of which is in the region of the end faces of the magnet. The magnet of the PCT application comprises approximately circular rings arranged one behind the other in the longitudinal direction. The rings have different inside diameters increasing towards the center of the magnet, whereby the homogeneity of the magnetic field in the interior is increased and a smaller overall length is achieved than with a magnet having a constant inside diameter. Each ring consists of several similar trapezoidal magnetized segments so that the cross sections of the opening of the magnet and the outer contour thereof are equilateral polygons, thereby giving the magnet approximately the form of a hollow cylinder. During the assembly of the magnet, gaps between the segments must be maintained for adjusting the positions of the segments. Accordingly, the segments of a ring do not engage each other. Because of these gaps, however, the intensity of the magnetic field in the cavity or opening of the magnet is not as great as the field generated in the case of a gapless cylindrical magnet made of permanent magnet material. A magnetic potential drop occurs in the gaps between the segments. In addition, the undesirable stray field due to the gaps is greater in the vicinity of the cylinder surface.

The manufacture of the above-described magnet is expensive in part because the procedures of magnetizing the segments and assembling them into a ring are complicated. The segments each consist of a permanent magnet material with a preferred orientation. Each segment is magnetized in the preferred orientation before the segments are joined together in a ring. The preferred orientation in each segment is different and depends on the location of the center of the segment upon assembly of the magnet. For this reason every segment must be magnetized separately.

Upon magnetization, each segment is held for assembly by a frame which has a fine adjustment screw by which the final position of the segment can be adjusted. During assembly, all frames with their respective segments are brought into their end positions by means of special guides. In the process, large magnetic forces between the segments occur which must be intercepted by and transmitted through the guides. The magnetic fields of the segments also influence each other during the motions of the assembly process, with the result that the magnetic field may not be sufficiently homogeneous in the patient receiving cavity. To correct the magnetic field in the cavity, the positions of all segments are varied by means of the fine adjustment screws. For each segment, several measurements and correction calculations by a data processing installation are necessary. After these corrections have been made, the segments are fixed in their positions and the frames are removed. In this manner one of the rings arranged in tandem is completed. Subsequently this ring is placed in a support frame. This procedure is repeated for each following ring and the positions of the rings in the support frame are fixed by further measurements and calculations.

An object of the present invention is to provide an improved magnet of permanent magnet material with a homogeneous field of the above-described type.

Another object of the present invention is to provide such a magnet which is simply manufactured.

SUMMARY OF THE INVENTION

According to the invention, a magnet for use in nuclear spin tomograph has an opening or cavity and an outer contour which are substantially rectangular. Two horizontal legs in the form of rectangular prisms extend perpendicularly to the approximately homogeneous magnetic field generated in the magnet's cavity and to a pair of vertical legs also in the form of rectangular prisms. The four legs define the cavity and are coupled to each other by four prismatic connecting parts. The magnet, after it is assembled, is magnetized as a whole in such a manner that the magnetic field in the vertical legs is mainly parallel to but opposed in direction to the magnetic field in the cavity and is closed via the horizontal legs and the connecting parts. In addition, the magnetic flux density increases from the inside surfaces of the vertical legs toward the outer surfaces thereof.

Because the magnet cavity and the outer contour of a magnet pursuant to the present invention are substantially rectangular, the magnet has a geometrically simple form which can be assembled advantageously from commercially available prismatic blocks. Because of the lack of gaps in the circumferential direction, the utilization of the permanent magnet material is high, i.e., a strong magnetic field prevails in the cavity and the stray field in the spaced outside the magnet is small. Because the permanent magnet material is nonmagnetic during assembly, no magnetic forces occur between parts of the magnet during assembly and consequently no expensive fixtures are necessary. Because the magnetic field in the vertical legs extends mainly parallel, but in a direction opposite, to the homogeneous field in the magnet cavity and is closed via the horizontal legs and the prismatic connecting pieces, the magnetic flux density increasing from the inside surfaces of the vertical legs towards the outer surfaces thereof, the space outside of the magnet is approximately free of magnetic fields. This result indicates that the magnetic flux caused by the permanent magnet material permeates mainly the interior of the magnet.

Advantageously, on the inside surface of each horizontal leg is disposed a magnetically soft plate having on an inner surface facing the cavity thin, narrow sheet metal strips which do not cover the entire surface of the magnetically soft plates. The homogeneity of the magnetic field in the interior is enhanced by the magnetically soft plates inasmuch as the plates induce the formation of surfaces of the same magnetic potential. The thin and narrow magnetically soft sheet metal strips on the surfaces of the magnetically soft plates facing the magnet cavity serve to equalize small inhomogeneities of the magnetic field after magnetization. The magnetically soft plates can be simply made of sheet metal laminations extending in planes perpendicular to the longitudinal direction of the magnet. Such a use of laminations facilitates the shaping of the plates. Preferably, at least one of the magnetically soft plates has on the surface facing the cavity a cylindrical recess or concave curvature extending transversely to the longitudinal axis of the magnet. The recess or curvature increases the homogeneity of the magnetic field in the interior, whereby the overall length of the magnet can be shortened. The amount of magnetic material required is reduced if the magnet consists of magnetic material with preferred orientation.

DETAILED DESCRIPTION

Figure 1:
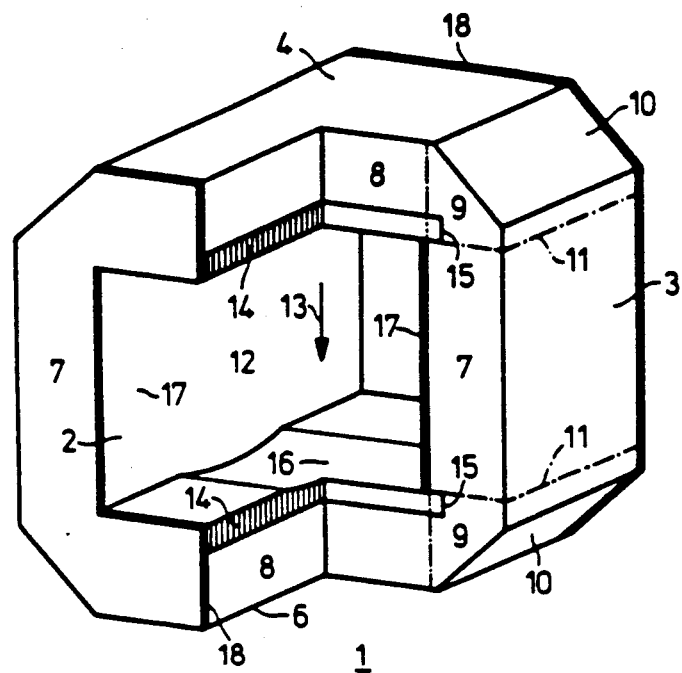
FIG. 1 is a perspective view of a magnet, partially in cross section, according to the invention.

A magnet 1 of a nuclear spin tomograph is substantially prismatic and has a rectangular opening 2 which extends longitudinally through magnet 1 and parallel to outer surfaces 3, 4, 5 and 6 of the magnet to form a prismatic cavity 12. Magnet 1 comprises two prismatic vertical legs 7, two prismatic horizontal legs 8, and four prismatic coupling elements 9 connecting the legs to each other. Magnet 1 advantageously consists of a ceramic-ferrite permanent magnet material which is magnetized upon assembly of the magnet from commercially available prismatic blocks. Vertical legs 7, horizontal legs 8 and coupling elements 9 are cemented to each other at their mutual contact surfaces 11 shown by dashed-dotted lines. This arrangement simplifies the assembly of magnet 1. In accordance with the invention, the magnetized permanent magnet material gaplessly surrounds cavity 12, which cavity is suitable for receiving an adult person (not shown). A substantially uniform or homogeneous magnetic field 13 oriented perpendicularly to the longitudinal axis of the magnet 1 prevails in cavity 12.

For homogenizing magnetic field 13, magnetically soft plates 14 oriented perpendicularly to magnetic field 13 are attached to the inner surfaces of horizontal legs 8 facing cavity 12. The two magnetically soft plates are wider than horizontal legs 8 and are placed in recesses 15 (indicated by dotted lines) in coupling elements 9. Recesses 15 are formed simply by omitting prismatic blocks of permanent magnet material at the corners of coupling elements 9 opposite beveled surfaces 10. Accordingly, all portions of magnet 1 deviating from a prismatic shape are formed in coupling elements 9 so that only those elements must be machined. This result is significant for simplifying fabrication of magnet 1 inasmuch as the permanent magnet material is mechanically very hard, and rework is concomitantly very expensive.

Magnetically soft plates 14 consist of metal sheets or laminations arranged one behind the other in the longitudinal direction. The lower of the two magnetically soft plates has a concave curvature or cylindrical recess 16 which aids in the homogenization of magnetic field 13 and thereby enables a reduction in the overall length of magnet 1 with respect to a magnet without the curvature or recess. Recess 16 is formed by providing successive metal laminations with heights decreasing towards a minimum at the middle of the magnet.

The formation of magnetically soft plates 14 as laminations simplifies fabrication of magnet 1 insofar as solid plates would require reworking for obtaining the curvature. Fabrication of magnet 1 is further simplified by providing magnetically soft plates 14 on horizontal legs 8, because recess 16 is easier to form in plates 14 than the mechanically hard horizontal legs 8 of permanent magnetic material. The magnetic forces acting between magnetically soft plates 14 are intercepted by and transmitted through nonmagnetic supports 17 disposed on the inner surfaces of vertical legs 7 and connected at the end faces of magnet 1 to nonmagnetic frames or facing members 18.

Figure 2:
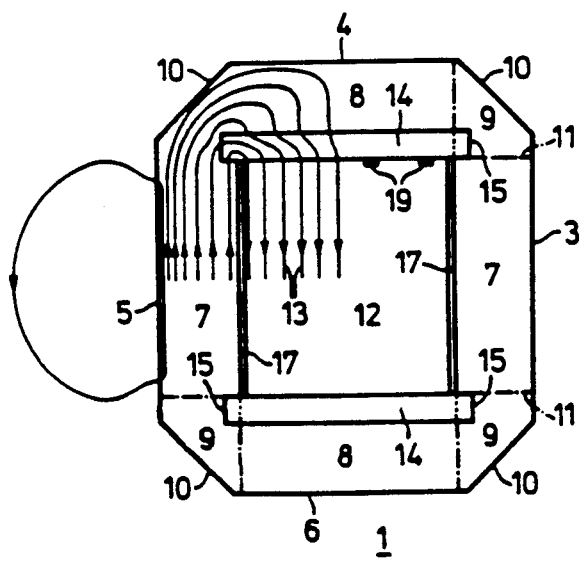
FIG. 2 is a front elevational view of the magnet of FIG. 1, with an end plate or frame element removed showing the field in the magnet in a plane extending transversely to the longitudinal direction is shown. Inasmuch as the transverse axes of the magnet are symmetry lines of the field pattern, the field pattern is shown only in one quarter of the magnet to simplify the drawing.

As shown in FIG. 2, magnet 1, consisting of a ceramic-ferrite permanent magnet material, is magnetized so that the magnetic field is conducted nearly exclusively in vertical legs 7, coupling elements 9, horizontal legs 8, magnetically soft plates 14, and cavity 12 of magnet 1. The space outside magnet 1 is substantially free of magnetic fields. In cavity 12, a homogeneous magnetic field 13 of 0.2 T prevails, while the magnetic field in the space outside of magnet 1 is only 0.01 T at a distance 0.5 m from surfaces 3 and 5. The magnetic field lines in vertical legs 7 are mainly parallel, and opposed in direction, to the magnetic field lines 13 in cavity 12. The magnetic flux density increases from the inner surfaces of vertical legs 7 towards outer surfaces 3 and 5 so that the flux density at the outer surfaces have nearly the value of the remanence of a ceramic-ferrite permanent magnetic material. The magnetic field is also approximately parallel to outer surfaces 4 and 6 and beveled surfaces 10, all of which represent boundary surfaces between different materials. The flux density at those boundary surfaces assumes the value of the remanence of the ceramic-ferrite permanent magnet material. Accordingly, the magnet field intensity is approximately zero at the boundaries with the result that the space outside magnet 1 is approximately free of fields.

Part of the magnetic flux in vertical legs 7 is transmitted via those portions of magnetically soft plates 14 which are imbedded in recesses 15 of the coupling elements 9. In this way, coupling elements 9 and horizontal legs 8 are magnetically relieved so that horizontal legs 8 can be narrower than vertical legs 7. A similarly high utilization of the ceramic-ferrite permanent magnet material is achieved in vertical legs 7. Magnetically soft plates 14 thus help save ceramic-ferrite permanent magnet material. Replacing the ceramic-ferrite permanent magnet material in horizontal legs 8 and coupling elements 9 by magnetically soft materials, however, would have the disadvantage that, with the same external dimensions, a weaker magnetic field would prevail in cavity 12 inasmuch as horizontal legs 8 would not contribute to the building up of the magnetic field, and the stray field in the space outside magnet 1 would be increased.

Upon assembly, magnet 1 is magnetized by a simple prismatic coil (not shown) energized with a current pulse. In cavity 12, a homogeneous magnetic field with a flux density of 2.7 T is obtained, and the remanence of the ceramic-ferrite permanent magnet material is exceeded in the magnet.

Because local variations in the properties of the ceramic-ferrite permanent magnet material within the different parts of magnet 1 cannot be avoided, which variations would cause inhomogeneity in magnetic field 13 to increase beyond a maximum permissible value, narrow sheet metal strips 19 are attached to the inside surfaces of magnetically soft plates 14. These strips 19 serve to correct the magnetic field in cavity 12 and are shown in FIG. 2 by way of example at the upper plate 14 only. The dimensions of strips 19, their orientations and their positions on the inside surfaces of plates 14 depend on random variations in the properties of the magnetic material. Their positions are calculated from measurements of magnetic field 13 after magnet 1 is magnetized. Exact positions can also be determined by simple tests instead of by calculation.

Magnet 1 is not limited to ceramic-ferrite permanent magnet material. Materials with higher remanence can be used, for instance, with a SmCo base in order to obtain higher flux densities in cavity 12. In addition, permanent magnet material with preferred orientation can be used to make magnet 1.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to understood that the descriptions and illustrations herein are proferred by way example to facilitate comprehension of the invention and should not be construed to limit the scope thereof.

What is claimed is:

1. A magnet for generating a substantially homogeneous magnetic field in a space large enough to receive a human patient, for use in a nuclear spin tomograph, said magnet comprising:

two mutually parallel first rectangular prisms spaced from one another;

two mutually parallel second rectangular prisms spaced from one another, said second rectangular prisms being disposed at opposite ends of and perpendicularly with respect to said first rectangular prisms, each of said prisms being made of a magnetized permanent magnetic material; and linking means including at least four elongate prismatic elements for coupling said prisms to each other to form an elongate body defining a substantially rectangular prismatic cavity with a longitudinal axis of symmetry, said elongate body having a cross-section with a substantially rectangular outer perimeter, each of said elongate prismatic elements serving to connect a respective pair of said prisms, said first rectangular prisms having respective inner surfaces defining said cavity and respective outer surfaces opposite said cavity, said prisms being permanently magnetized upon assembly of said elongate body so that field lines of a magnetic field in said first rectangular prisms are parallel to and oppositely directed with respect to field lines of a magnetic field in said cavity, so that the field lines of the magnetic field in said first rectangular prisms are connected to respective field lines of the magnetic field in said cavity via said elongate prismatic elements and via said second rectangular prisms, and so that the field lines in said first rectangular prisms have a density increasing from said inner surfaces toward said outer surfaces, said first rectangular prisms extending parallel to the magnetic field in said cavity and said second rectangular prisms extending perpendicularly with respect to the magnetic field in said cavity, the field lines of the magnetic field in said cavity being oriented perpendicularly with respect to said axis.

2. A magnet as defined in claim 1 wherein each of said second rectangular prisms have respective inner surfaces facing said cavity, further comprising two plates of magnetically soft material each disposed on a respective one of the inner surfaces of said second rectangular prisms, said plates having respective inner surfaces facing said cavity, further comprising a plurality of thin sheet metal strips disposed on the inner surfaces of said plates.

3. A magnet as defined in claim 2 wherein each of said plates is formed of a multiplicity of laminations located in respective planes extending perpendicularly to said axis and to said first rectangular prisms.

4. A magnet as defined in claim 2 or 3 wherein at least one of said plates is provided with a recess at the respective inner surface.

5. A magnet as defined in claim 4 wherein said recess is cylindrical and extends in a direction transverse to said axis.

6. A magnet as defined in claim 4 wherein said elongate prismatic elements have respective beveled outer surfaces.

7. A magnet as defined in claim 2 or 3 wherein said plates extend into recesses formed in said elongate prismatic elements.

8. A magnet as defined in claim 1 wherein said prisms are made of magnetic material with preferred orientation.

9. A magnet as defined in claim 1 wherein said prisms and said elongate prismatic elements are made of ceramic ferrite material.

10. A magnet for generating a substantially homogeneous magnetic field in a space large enough to receive a human patient, for use in a nuclear spin tomograph, said magnet comprising:

two mutually parallel first rectangular prisms spaced from one another;

two mutually parallel second rectangular prisms spaced from one another, said second rectangular prisms being disposed at opposite ends of and perpendicularly with respect to said first rectangular prisms, each of said prisms being made of a magnetized permanent magnetic material;

linking means including at least four elongate prismatic elements for coupling said prisms to each other to form an elongate body defining a substantially rectangular prismatic cavity with a longitudinal axis of symmetry, said elongate body having a cross-section with a substantially rectangular outer perimeter, each of said elongate prismatic elements serving to connect a respective pair of said prisms, said first rectangular prisms having respective inner surfaces defining said cavity and respective outer surfaces opposite said cavity, each of said second rectangular prisms having respective inner surfaces facing said cavity, said prisms being permanently magnetized upon assembly of said elongate body so that field lines of a magnetic field in said first rectangular prisms are parallel to and oppositely directed with respect to field lines of a magnetic field in said cavity, so that the field lines of the magnetic field in said first rectangular prisms are connected to respective field lines of the magnetic field in said cavity via said elongate prismatic elements and via said second rectangular prisms, and so that the field lines in said first rectangular prisms have a density increasing from the inner surfaces of said first rectangular prisms toward said outer surfaces, said first rectangular prisms extending parallel to the magnetic field in said cavity and said second rectangular prisms extending perpendicularly with respect to the magnetic field in said cavity, the field lines of the magnetic field in said cavity being oriented perpendicularly with respect to said axis;

two plates of magnetically soft material each disposed on a respective one of the inner surfaces of said second rectangular prisms, said plates having respective inner surfaces facing said cavity; each of said plates being formed of a multiplicity of laminations located in respective planes extending perpendicularly to said axis and to said first rectangular prisms; and a plurality of thin sheet metal strips disposed on the inner surfaces of said plates.

11. A magnet as defined in claim 10 wherein at least one of said plates is provided with a cylindrical concavity extending in a direction transverse to said axis.

12. A magnet as defined in claim 10 wherein said elongate prismatic elements have respective beveled outer surfaces.

13. In a magnet for use in a nuclear spin tomograph, the improvement wherein said magnet is an elongate body defining a substantially rectangular prismatic cavity with a longitudinal axis of symmetry, said elongate body having a cross-section with a substantially rectangular outer perimeter, said body being formed of permanent magnetic material magnetized upon formation of said body to provide a substantially uniform relatively large magnetic field in said cavity and a relatively small magnetic field outside said body.

14. A method for manufacturing a magnet for use in a nuclear spin tomograph, said magnet generating a substantially homogeneous magnetic field in a space large enough to receive a human patient, said method comprising the steps of:

providing two mutually parallel first rectangular prisms of a magnetizable material;

providing two mutually parallel second rectangular prisms of a magnetizable material;

coupling said prisms to each other by means of at least four elongate prismatic connecting elements to form an elongate body defining a substantially rectangular prismatic cavity with a longitudinal axis of symmetry, said first rectangular prisms being parallel to and spaced from one another, said second rectangular prisms being parallel to and spaced from one another, said second rectangular prisms being disposed at opposite ends of and perpendicularly with respect to said first rectangular prisms, said elongate body having a cross-section with a substantially rectangular outer perimeter, each of said elongate prismatic elements serving to connect a respective pair of said prisms; and permanently magnetizing said prisms upon assembly of said elongate body so that field lines of a magnetic field in said first rectangular prisms are parallel to and oppositely directed with respect to field lines of a magnetic field in said cavity, so that the field lines of the magnetic field in said first rectangular prisms are connected to respective field lines of the magnetic field in said cavity via said elongate prismatic elements and via said second rectangular prisms, and so that the field lines in said first rectangular prisms have a density increasing from said inner surfaces toward said outer surfaces, said first rectangular prisms extending parallel to the magnetic field in said cavity and said second rectangular prisms extending perpendicularly with respect to the magnetic field in said cavity, the field lines of the magnetic field in said cavity being oriented perpendicularly with respect to said axis.

* * * * *